US009279138B2

(12) United States Patent
Hoshino et al.

(10) Patent No.: US 9,279,138 B2
(45) Date of Patent: Mar. 8, 2016

(54) VITAMIN C PRODUCTION IN A MICROORGANISM, GLUCONOBACTER

(75) Inventors: Tatsuo Hoshino, Kamakura (JP); Masako Shinjoh, Kanagawa (JP); Christine Toepfer, Murg (DE); Noribumi Tomiyama, Fujisawa (JP)

(73) Assignee: DSM ASSETS B.V., Heerlen (NL)

( * ) Notice: Subject to any disclaimer, the term of this patent is extended or adjusted under 35 U.S.C. 154(b) by 1542 days.

(21) Appl. No.: 11/883,830

(22) PCT Filed: Feb. 10, 2006

(86) PCT No.: PCT/EP2006/001203
§ 371 (c)(1),
(2), (4) Date: Sep. 20, 2007

(87) PCT Pub. No.: WO2006/084708
PCT Pub. Date: Aug. 17, 2006

(65) Prior Publication Data
US 2009/0142815 A1    Jun. 4, 2009

(30) Foreign Application Priority Data
Feb. 11, 2005  (EP) .................................... 05405066
Feb. 11, 2005  (EP) .................................... 05405112

(51) Int. Cl.
*C12P 17/04* (2006.01)
*C12N 9/02* (2006.01)
*C12P 1/04* (2006.01)

(52) U.S. Cl.
CPC ............... *C12P 17/04* (2013.01); *C12N 9/0008* (2013.01); *C12P 1/04* (2013.01)

(58) Field of Classification Search
CPC .... C12N 9/0008; C12N 15/74; C12N 9/0004; C12N 9/0053; C12N 15/102; C12N 15/52; C12Y 101/99012; C12P 17/04; C12P 7/60; C12P 17/00; C12P 7/24; C12P 7/26
See application file for complete search history.

(56) References Cited

U.S. PATENT DOCUMENTS

| | | | | |
|---|---|---|---|---|
| 5,817,490 | A | * | 10/1998 | Hubbs ............................ 435/137 |
| 5,861,292 | A | * | 1/1999 | Niwa et al. ..................... 435/190 |
| 2006/0035349 | A1 | | 2/2006 | Hoshino et al. |
| 2006/0121582 | A1 | | 6/2006 | Hoshino et al. |
| 2007/0161093 | A1 | | 7/2007 | Hoshino et al. |

FOREIGN PATENT DOCUMENTS

WO    WO 2004/029235    *    4/2010

OTHER PUBLICATIONS

Hancock et al., 2002, Trends in Biotechnology, 20: 299-305.*
Li et al., 1999, FEBS, 456, 13-16.*
Loewus et al., 1990, Plant Physiol. 94: 1492-1495.*
Miyazaki et al., 2006, Applied and Environmental Microbiology, 72: 1487-1495.*
Aiguo et al., 1998, Biotechnology, 20: 939-942.*
Skolnick et al, TIBTECH, 2000, 18:34-39.*
Rychlik et al, Nuc Acids Res, 1990, 18:6409-6412.*
Seffernick et al, J Bacteriology, 2001, 183:2405-2410.*
Wells, Biochemistry, 1990, 29:8509-8517.*
Bowie et al, Science, 1990, 247:1306-1310.*
International Search Report for related Appln. No. PCT/EP2006/001203, completed May 2006.
Written Opinion for related Appln. No. PCT/EP2006/001203, five pages, completed May 2006.
Database UniProt [Online] "L-sorbosone dehydrogenase, NAD(P) dependent" retrieved from EBI accession No. UNIPROT: Q47943, Database accession No. Q47943 (Nov. 1996).
Saito et al. "Cloning of genes coding for L-sorbose and L-sorbosone dehydrogenases from *Gluconobacter oxydans* and microbial production of 2-keto-L-gulonate, a precursor of L-ascorbic acid, in a recombinant *G. oxydans* strain" Applied and Environmental Microbiology, vol. 63, No. 2, pp. 454-460 (Feb. 1997).

* cited by examiner

*Primary Examiner* — Deborah Crouch
*Assistant Examiner* — Magdalene Sgagias
(74) *Attorney, Agent, or Firm* — Nixon & Vanderhye P.C.

(57) ABSTRACT

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of the polynucleotides and polypeptides as biotechnological tools in the production of Vitamin C from microorganisms, whereby a modification of the polynucleotides and/or encoded polypeptides has a direct or indirect impact on yield, production, and/or efficiency of production of the fermentation product in the microorganism. Also included are methods/processes of using the polynucleotides and modified polynucleotide sequences to transform host microorganisms. The invention also relates to genetically engineered microorganisms and their use for the direct production of Vitamin C.

7 Claims, No Drawings

SEQUENCE LISTING

```
<160> NUMBER OF SEQ ID NOS: 4

<210> SEQ ID NO 1
<211> LENGTH: 1497
<212> TYPE: DNA
<213> ORGANISM: Gluconobacter oxydans DSM 17078

<400> SEQUENCE: 1
atgaatgttg tctcaaagac tgtatcttta ccgttaaagc cgcgtgagtt cggattctat      60
attgatggag aatggcgcgc aggtaaggat ttcttcgatc gttcctcgcc ggctcatgat     120
```

-continued

```
gttcccgtca cccgtattcc acgctgcacc cgtgaggacc ttgatgaggc agtcgctgct    180
gcacgtcgtg ctttcgagaa cggaagctgg tcgggcctgg cggccgcgga tcgtgcggcg    240
gttcttctga agccgcgggc ccttctgcgc gagcgccgcg atgacatcgc ttactgggaa    300
gttctcgaaa acgggaagcc catcagccag gcgaagggcg agatcgatca ctgtatcgcc    360
tgtttcgaga tggcggccgg cgctgcgcgg atgctgcatg gtgatacgtt caacaatctg    420
ggcgaggggc tgttcggcat ggtcctgcgg gagcccatcg tgtcgtcgg tctgattacg     480
ccgtggaact tcccgttcat gatcctgtgt gagcgcgcgc ctttcattct cgcatccggc    540
tgcacgctgg tcgtcaagcc tgccgaagtc acgagtgcca cgacgcttct tctggcggaa    600
gtgctggcgg atgcggggct gccgaagggt gtcttcaatg ttgtgacggg cacggggcgc    660
acggtcgggc aggccatgac cgagcatcag gacatcgaca tgctgtcctt cacgggctcc    720
acgggcgtcg gcaagtcctg catccatgcg gcggctgaca gcaacctgaa gaaactgggc    780
cttgagcttg gcggcaagaa cccgatcgtc gtgttcgctg acagcaacct tgaggatgcg    840
gccgatgcgg tagctttcgg gattagtttc aacaccgggc agtgctgtgt gtcgtcgagc    900
cgcctgattg tagagcggtc cgtggccgag aagttcgagc gtctcgttgt ggcgaaaatg    960
gagaagatcc gcgtcggcga tccgttcgat cctgagacgc agatcggcgc cattacgacg   1020
gaagcgcaga acaagaccat tctggactat atcgccaagg gcaaggccga gggcgccagg   1080
ctgctctgcg gtggcgggat cgtcgatttc ggcaaagggc agtatatcca gccgacgctt   1140
ttcacggatg tgaagccctc gatgggcatc gcgcgtgacg agattttgg gccggtcctg    1200
gcgtccttcc acttcgatac cgtcgatgag gcgatcgcga ttgccaatga cacggtttac   1260
ggcctggccg catcggtctg gagcaaggat atcgacaagg cgcttgccgt gacccgtcgt   1320
gttcgcgctg ccgcttctg ggtgaacacc atcatgagcg gtggtcccga cgccgctg     1380
ggtggtttca gcagtcggg ctggggccgt gaggccggtc tgtacggcgt tgaggaatat   1440
acgcagatca aatctgtcca tatcgaaact ggcaaacgtt cgcactggat ttcgtaa      1497
```

<210> SEQ ID NO 2
<211> LENGTH: 498
<212> TYPE: PRT
<213> ORGANISM: Gluconobacter oxydans DSM 17078

<400> SEQUENCE: 2

```
Met Asn Val Val Ser Lys Thr Val Ser Leu Pro Leu Lys Pro Arg Glu
1               5                   10                  15

Phe Gly Phe Tyr Ile Asp Gly Glu Trp Arg Ala Gly Lys Asp Phe Phe
            20                  25                  30

Asp Arg Ser Ser Pro Ala His Asp Val Pro Val Thr Arg Ile Pro Arg
        35                  40                  45

Cys Thr Arg Glu Asp Leu Asp Glu Ala Val Ala Ala Arg Arg Ala
    50                  55                  60

Phe Glu Asn Gly Ser Trp Ser Gly Leu Ala Ala Asp Arg Ala Ala
65                  70                  75                  80

Val Leu Leu Lys Ala Ala Gly Leu Leu Arg Glu Arg Arg Asp Asp Ile
            85                  90                  95

Ala Tyr Trp Glu Val Leu Glu Asn Gly Lys Pro Ile Ser Gln Ala Lys
            100                 105                 110

Gly Glu Ile Asp His Cys Ile Ala Cys Phe Glu Met Ala Ala Gly Ala
        115                 120                 125
```

Ala Arg Met Leu His Gly Asp Thr Phe Asn Asn Leu Gly Glu Gly Leu
130                 135                 140

Phe Gly Met Val Leu Arg Glu Pro Ile Gly Val Val Gly Leu Ile Thr
145                 150                 155                 160

Pro Trp Asn Phe Pro Phe Met Ile Leu Cys Glu Arg Ala Pro Phe Ile
                165                 170                 175

Leu Ala Ser Gly Cys Thr Leu Val Val Lys Pro Ala Glu Val Thr Ser
                180                 185                 190

Ala Thr Thr Leu Leu Leu Ala Glu Val Leu Ala Asp Ala Gly Leu Pro
                195                 200                 205

Lys Gly Val Phe Asn Val Val Thr Gly Thr Gly Arg Thr Val Gly Gln
210                 215                 220

Ala Met Thr Glu His Gln Asp Ile Asp Met Leu Ser Phe Thr Gly Ser
225                 230                 235                 240

Thr Gly Val Gly Lys Ser Cys Ile His Ala Ala Asp Ser Asn Leu
                245                 250                 255

Lys Lys Leu Gly Leu Glu Leu Gly Gly Lys Asn Pro Ile Val Val Phe
                260                 265                 270

Ala Asp Ser Asn Leu Glu Asp Ala Ala Asp Ala Val Ala Phe Gly Ile
                275                 280                 285

Ser Phe Asn Thr Gly Gln Cys Cys Val Ser Ser Arg Leu Ile Val
                290                 295                 300

Glu Arg Ser Val Ala Glu Lys Phe Glu Arg Leu Val Val Ala Lys Met
305                 310                 315                 320

Glu Lys Ile Arg Val Gly Asp Pro Phe Asp Pro Glu Thr Gln Ile Gly
                325                 330                 335

Ala Ile Thr Thr Glu Ala Gln Asn Lys Thr Ile Leu Asp Tyr Ile Ala
                340                 345                 350

Lys Gly Lys Ala Glu Gly Ala Arg Leu Leu Cys Gly Gly Gly Ile Val
                355                 360                 365

Asp Phe Gly Lys Gly Gln Tyr Ile Gln Pro Thr Leu Phe Thr Asp Val
                370                 375                 380

Lys Pro Ser Met Gly Ile Ala Arg Asp Glu Ile Phe Gly Pro Val Leu
385                 390                 395                 400

Ala Ser Phe His Phe Asp Thr Val Asp Glu Ala Ile Ala Ile Ala Asn
                405                 410                 415

Asp Thr Val Tyr Gly Leu Ala Ala Ser Val Trp Ser Lys Asp Ile Asp
                420                 425                 430

Lys Ala Leu Ala Val Thr Arg Arg Val Arg Ala Gly Arg Phe Trp Val
                435                 440                 445

Asn Thr Ile Met Ser Gly Gly Pro Glu Thr Pro Leu Gly Gly Phe Lys
                450                 455                 460

Gln Ser Gly Trp Gly Arg Glu Ala Gly Leu Tyr Gly Val Glu Glu Tyr
465                 470                 475                 480

Thr Gln Ile Lys Ser Val His Ile Glu Thr Gly Lys Arg Ser His Trp
                485                 490                 495

Ile Ser

<210> SEQ ID NO 3
<211> LENGTH: 20
<212> TYPE: DNA
<213> ORGANISM: Artificial Sequence
<220> FEATURE:
<223> OTHER INFORMATION: primer

```
<400> SEQUENCE: 3
atgaatgttg tctcaaagac                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttacgaaatc cagtgcgaac                                              20
```

VITAMIN C PRODUCTION IN A MICROORGANISM, GLUCONOBACTER

This application is a U.S. national stage of International Patent Application No. PCT/EP2006/001203, filed 10 Feb. 2006, which designated the U.S. and claims priority benefit of EP 05405112.3, filed 11 Feb. 2005, and EP 05405066.1, filed 11 Feb. 2005; the entire contents of each of which are hereby incorporated by reference.

The present invention relates to newly identified genes that encode proteins that are involved in the synthesis of L-ascorbic acid (hereinafter also referred to as Vitamin C). The invention also features polynucleotides comprising the full-length polynucleotide sequences of the novel genes and fragments thereof, the novel polypeptides encoded by the polynucleotides and fragments thereof, as well as their functional equivalents. The present invention also relates to the use of said polynucleotides and polypeptides as biotechnological tools in the production of Vitamin C from microorganisms, whereby a modification of said polynucleotides and/or encoded polypeptides has a direct or indirect impact on yield, production, and/or efficiency of production of the fermentation product in said microorganism. Also included are methods/processes of using the polynucleotides and modified polynucleotide sequences to transform host microorganisms. The invention also relates to genetically engineered microorganisms and their use for the direct production of Vitamin C.

Vitamin C is one of very important and indispensable nutrient factors for human beings. Vitamin C is also used in animal feed even though some farm animals can synthesize it in their own body.

For the past 70 years, Vitamin C has been produced industrially from D-glucose by the well-known Reichstein method. All steps in this process are chemical except for one (the conversion of D-sorbitol to L-sorbose), which is carried out by microbial conversion. Since its initial implementation for industrial production of Vitamin C, several chemical and technical modifications have been used to improve the efficiency of the Reichstein method. Recent developments of Vitamin C production are summarized in Ullmann's Encyclopedia of Industrial Chemistry, $5^{th}$ Edition, Vol. A27 (1996), pp. 547ff.

Different intermediate steps of Vitamin C production have been performed with the help of microorganisms or enzymes isolated therefrom. Thus, 2-keto-L-gulonic acid (2-KGA), an intermediate compound that can be chemically converted into Vitamin C by means of an alkaline rearrangement reaction, may be produced by a fermentation process starting from L-sorbose or D-sorbitol, by means of strains belonging e.g. to the *Ketogulonicigenium* or *Gluconobacter* genera, or by an alternative fermentation process starting from D-glucose, by means of recombinant strains belonging to the *Gluconobacter* or *Pantoea* genera.

Current chemical production methods for Vitamin C have some undesirable characteristics such as high-energy consumption and use of large quantities of organic and inorganic solvents. Therefore, over the past decades, other approaches to manufacture Vitamin C using microbial conversions, which would be more economical as well as ecological, have been investigated.

Direct Vitamin C production from a number of substrates including D-sorbitol, L-sorbose and L-sorbosone has been reported in several microorganisms, such as algae, yeast and acetic acid bacteria, using different cultivation methods. Examples of known bacteria able to directly produce Vitamin C include, for instance, strains from the genera of *Gluconobacter, Gluconacetobacter, Acetobacter, Ketogulonicigenium, Pantoea, Pseudomonas* or *Escherichia*. Examples of known yeast or algae include, e.g. *Candida, Saccharomyces, Zygosaccharomyces, Schizosaccharomyces, Kluyveromyces* or *Chlorella*.

Microorganisms able to assimilate D-sorbitol for growth usually possess enzymes able to oxidize this compound into a universal assimilation substrate such as D-fructose. Also microorganisms able to grow on L-sorbose possess an enzyme, NAD(P)H-dependent L-sorbose reductase, which is able to reduce this compound to D-sorbitol, which is then further oxidized into D-fructose. D-fructose is an excellent substrate for the growth of many microorganisms, after it has been phosphorylated by means of a D-fructose kinase.

For instance, in the case of acetic acid bacteria, which are obligate aerobe, gram-negative microorganisms belonging to the genus *Acetobacter, Gluconobacter,* and *Gluconacetobacter*, these microorganisms are able to transport D-sorbitol into the cytosol and convert it into D-fructose by means of a cytosolic NAD-dependent D-sorbitol dehydrogenase. Some individual strains, such as *Gluconobacter oxydans* IFO 3292, and IFO 3293, are able as well to transport L-sorbose into the cytosol and reduce it to D-sorbitol by means of a cytosolic NAD(P)H-dependent L-sorbose reductase, which then is further oxidized into D-fructose. In these bacteria, the Embden-Meyerhof-Parnas pathway, as well as the tricarboxyclic acid cycle are not fully active, and the main pathway channeling sugars into the central metabolism is the pentose phosphate pathway. D-fructose-6-phosphate, obtained from D-fructose by a phosphorylation reaction enters the pentose phosphate pathway, being further metabolized and producing reducing power in the form of NAD(P)H and tricarboxylic compounds necessary for growth and maintenance.

Acetic acid bacteria are well known for their ability to incompletely oxidize different substrates such as alcohols, sugars, sugar alcohols and aldehydes. These processes are generally known as oxidative fermentations or incomplete oxidations, and they have been well established for a long time in the food and chemical industry, especially in vinegar and in L-sorbose production. A useful product known to be obtained from incomplete oxidations of D-sorbitol or L-sorbose using strains belonging to the *Gluconobacter* genus is 2-KGA.

Acetic acid bacteria accomplish these incomplete oxidation reactions by means of different dehydrogenases located either in the periplasmic space, on the periplasmic membrane as well as in the cytoplasm. Different co-factors are employed by the different dehydrogenases, the most common being PQQ and FAD for membrane-bound or periplasmic enzymes, and NAD/NADP for cytoplasmic enzymes.

While all products of these oxidation reactions diffuse back to the external aqueous environment through the outer membrane, some of them can be passively or actively transported into the cell and be further used in metabolic pathways responsible for growth and energy formation. Inside the cell, oxidized products can many times be reduced back to their original substrate by means of reductases, and then be channeled back to the central metabolism.

Proteins, in particular enzymes and transporters, that are active in the metabolization of D-sorbitol or L-sorbose are herein referred to as being involved in the Sorbitol/Sorbose Metabolization System. Such proteins are abbreviated herein as SMS proteins and function in the direct metabolization of D-sorbitol or L-sorbose.

Metabolization of D-sorbitol or L-sorbose includes on one side the assimilation of these compounds into the cytosol and further conversion into metabolites useful for assimilation pathways such as the Embden-Meyerhof-Parnas pathway, the pentose phosphate pathway, the Entner-Doudoroff pathway, and the tricarboxyclic acid cycle, all of them involved in all vital energy-forming and anabolic reactions necessary for growth and maintenance of living cells. On the other side, metabolization of D-sorbitol or L-sorbose also includes the conversion of these compounds into further oxidized products such as L-sorbosone, 2-KGA and Vitamin C by so-called incomplete oxidation processes.

An object of the present invention is to improve the yields and/or productivity of Vitamin C production.

Surprisingly, it has now been found that SMS proteins or subunits of such proteins having activity towards or which are involved in the assimilation or conversion of D-sorbitol, L-sorbose or L-sorbosone play an important role in the biotechnological production of Vitamin C.

In one embodiment, SMS proteins of the present invention are selected from oxidoreductases [EC 1], preferably oxidoreductases acting on the CH—OH group of donors [EC 1.1], more preferably oxidoreductases with $NAD^+$ or $NADP^+$ as acceptor [EC 1.1.1] and oxidoreductases with other acceptors [EC 1.1.99], most preferably selected from oxidoreductases belonging to enzyme classes [EC 1.1.1.1], [EC 1.1.1.15] or [EC 1.2.1.-], or preferably oxidoreductases acting on the aldehyde or oxo group of donors [EC 1.2], more preferably oxidoreductases with $NAD^+$ or $NADP^+$ as acceptor [EC 1.2.1].

Furthermore, the SMS proteins of the present invention may be selected from the group consisting of membrane-bound PQQ-dependent D-sorbitol dehydrogenase, membrane-bound L-sorbose dehydrogenase, membrane-bound L-sorbosone dehydrogenase, membrane-bound FAD-dependent D-sorbitol dehydrogenase, cytosolic NAD-dependent D-sorbitol dehydrogenase, NAD(P)-dependent D-sorbitol dehydrogenase (also called as NADPH-dependent sorbose reductase), NAD-dependent xylitol dehydrogenase, NAD-dependent alcohol dehydrogenase, membrane-bound L-sorbose dehydrogenase, NAD(P)H-dependent L-sorbose reductase, cytosolic NADP-dependent sorbosone dehydrogenase, cytosolic NAD(P)H-dependent L-sorbosone reductase, membrane-bound aldehyde dehydrogenase, cytosolic aldehyde dehydrogenase, glycerol-3-phosphate dehydrogenase, glyceraldehyde-3-phosphate dehydrogenase, and others involved in SMS.

In particular, it has now been found that SMS proteins encoded by polynucleotides having a nucleotide sequence that hybridizes preferably under highly stringent conditions to a sequence shown in SEQ ID NO:1 play an important role in the biotechnological production of Vitamin C. It has also been found, that by genetically altering the expression level of nucleotides according to the invention in a microorganism capable of directly producing Vitamin C, such as for example *Gluconobacter*, the direct fermentation of Vitamin C by said microorganism can be even greatly improved.

Consequently, the invention relates to a polynucleotide selected from the group consisting of:
(a) polynucleotides encoding a polypeptide comprising the amino acid sequence according to SEQ ID NO:2;
(b) polynucleotides comprising the nucleotide sequence according to SEQ ID NO:1;
(c) polynucleotides comprising a nucleotide sequence obtainable by nucleic acid amplification such as polymerase chain reaction, using genomic DNA from a microorganism as a template and a primer set according to SEQ ID NO:3 and SEQ ID NO:4;
(d) polynucleotides comprising a nucleotide sequence encoding a fragment or derivative of a polypeptide encoded by a polynucleotide of any of (a) to (c) wherein in said derivative one or more amino acid residues are conservatively substituted compared to said polypeptide, and said fragment or derivative has the activity of an oxidoreductase [EC 1], preferably an oxidoreductase acting on the aldehyde or oxo group of donors [EC 1.2] (SMS 05);
(e) polynucleotides the complementary strand of which hybridizes under stringent conditions to a polynucleotide as defined in any one of (a) to (d) and which encode an oxidoreductase [EC 1], preferably an oxidoreductase acting on the aldehyde or oxo group of donors [EC 1.2] (SMS 05); and
(f) polynucleotides which are at least 70%, such as 85, 90 or 95% identical to a polynucleotide as defined in any one of (a) to (d) and which encode an oxidoreductase [EC 1], preferably an oxidoreductase acting on the aldehyde or oxo group of donors [EC 1.2] (SMS 05);
or
the complementary strand of such a polynucleotide.

The SMS protein as isolated from *Gluconobacter oxydans* DSM 17078 shown in SEQ ID NO:2 and described herein was found to be a particularly useful SMS protein, since it appeared that it performs a crucial function in the direct Vitamin C production in microorganisms, in particular in bacteria, such as acetic acid bacteria, such as *Gluconobacter*, *Acetobacter* and *Gluconacetobacter*. Accordingly, the invention relates to a polynucleotide encoding a polypeptide according to SEQ ID NO:2. This protein may be encoded by a nucleotide sequence as shown in SEQ ID NO:1. The invention therefore also relates to polynucleotides comprising the nucleotide sequence according to SEQ ID NO:1.

The nucleotide and amino acid sequences determined above were used as a "query sequence" to perform a search with Blast2 program (version 2 or BLAST from National Center for Biotechnology [NCBI] against the database PRO SW-SwissProt (full release plus incremental updates). From the searches, the SMS 05 polynucleotide according to SEQ ID NO:1 was annotated as encoding a NAD(P)-dependent sorbosone dehydrogenase.

A nucleic acid according to the invention may be obtained by nucleic acid amplification using cDNA, mRNA or alternatively, genomic DNA, as a template and appropriate oligonucleotide primers such as the nucleotide primers according to SEQ ID NO:3 and SEQ ID NO:4 according to standard PCR amplification techniques. The nucleic acid thus amplified may be cloned into an appropriate vector and characterized by DNA sequence analysis.

The template for the reaction may be cDNA obtained by reverse transcription of mRNA prepared from strains known or suspected to comprise a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

Accordingly, the invention relates to polynucleotides comprising a nucleotide sequence obtainable by nucleic acid amplification such as polymerase chain reaction, using DNA such as genomic DNA from a microorganism as a template and a primer set according to SEQ ID NO:3 and SEQ ID NO:4.

The invention also relates to polynucleotides comprising a nucleotide sequence encoding a fragment or derivative of a polypeptide encoded by a polynucleotide as described herein wherein in said derivative one or more amino acid residues are conservatively substituted compared to said polypeptide, and said fragment or derivative has the activity of a SMS polypeptide, preferably a SMS 05 polypeptide.

The invention also relates to polynucleotides the complementary strand of which hybridizes under stringent conditions to a polynucleotide as defined herein and which encode a SMS polypeptide, preferably a SMS 05 polypeptide.

The invention also relates to polynucleotides which are at least 70% identical to a polynucleotide as defined herein and which encode a SMS polypeptide; and the invention also relates to polynucleotides being the complementary strand of a polynucleotide as defined herein above.

The invention also relates to microorganisms wherein the activity of a SMS polypeptide, preferably a SMS 05 polypeptide, is reduced or abolished so that the yield of Vitamin C which is directly produced from D-sorbitol or L-sorbose is increased.

The skilled person will know how to reduce or abolish the activity of a SMS protein, preferably a SMS 05 protein. Such may be for instance accomplished by either genetically modifying the host organism in such a way that it produces less or no copies of the SMS protein, preferably the SMS 05 protein, than the wild type organism or by decreasing or abolishing the specific activity of the SMS protein, preferably the SMS 05 protein.

In the following description, procedures are detailed to achieve this goal, i.e. the increase in the yield and/or production of Vitamin C which is directly produced from D-sorbitol or L-sorbose by reducing or abolishing the activity of a SMS 05 protein. These procedures apply mutatis mutandis for other SMS proteins.

Modifications in order to have the organism produce less or no copies of the SMS 05 gene and/or protein may include the use of a weak promoter, or the mutation (e.g. insertion, deletion or point mutation) of (parts of) the SMS 05 gene or its regulatory elements. Decreasing or abolishing the specific activity of a SMS 05 protein may also be accomplished by methods known in the art. Such methods may include the mutation (e.g. insertion, deletion or point mutation) of (parts of) the SMS 05 gene.

Also known in the art are methods of reducing or abolishing the activity of a given protein by contacting the SMS 05 protein with specific inhibitors or other substances that specifically interact with the SMS 05 protein. In order to identify such specific inhibitors, the SMS 05 protein may be expressed and tested for activity in the presence of compounds suspected to inhibit the activity of the SMS 05 protein. Potential inhibiting compounds may for instance be monoclonal or polyclonal antibodies against the SMS 05 protein. Such antibodies may be obtained by routine immunization protocols of suitable laboratory animals.

The invention may be performed in any microorganism carrying a SMS 05 gene or homologue thereof. Suitable microorganisms may be selected from the group consisting of yeast, algae and bacteria, either as wild type strains, mutant strains derived by classic mutagenesis and selection methods or as recombinant strains. Examples of such yeast may be, e.g., *Candida*, *Saccharomyces*, *Zygosaccharomyces*, *Schizosaccharomyces*, or *Kluyveromyces*. An example of such algae may be, e.g., *Chlorella*. Examples of such bacteria may be, e.g., *Gluconobacter*, *Acetobacter*, *Gluconacetobacter*, *Ketogulonicigenium*, *Pantoea*, *Pseudomonas*, such as, e.g., *Pseudomonas putida*, and *Escherichia*, such as, e.g., *Escherichia coli*. Preferred are *Gluconobacter* or *Acetobacter aceti*, such as for instance *G. oxydans*, *G. cerinus*, *G. frateurii*, *A. aceti* subsp. *xylinum* or *A. aceti* subsp. *orleanus*, preferably *G. oxydans* DSM 17078. *Gluconobacter oxydans* DSM 17078 (formerly known as *Gluconobacter oxydans* N44-1) has been deposited at Deutsche Sammlung von Mikroorganismen und Zellkulturen (DSMZ), Mascheroder Weg 1B, D-38124 Braunschweig, Germany according to the Budapest Treaty on 26, Jan. 2005.

Microorganisms which can be used for the present invention may be publicly available from different sources, e.g., Deutsche Sammlung von Mikroorganismen und Zellkulturen (DSMZ), Mascheroder Weg 1B, D-38124 Braunschweig, Germany, American Type Culture Collection (ATCC), P.O. Box 1549, Manassas, Va. 20108 USA or Culture Collection Division, NITE Biological Resource Center, 2-5-8, Kazusakamatari, Kisarazu-shi, Chiba, 292-0818, Japan (formerly: Institute for Fermentation, Osaka (IFO), 17-85, Jusohonmachi 2-chome, Yodogawa-ku, Osaka 532-8686, Japan). Examples of preferred bacteria deposited with IFO are for instance *Gluconobacter oxydans* (formerly known as *G. melanogenus*) IFO 3293, *Gluconobacter oxydans* (formerly known as *G. melanogenus*) IFO 3292, *Gluconobacter oxydans* (formerly known as *G. rubiginosus*) IFO 3244, *Gluconobacter frateurii* (formerly known as *G. industrius*) IFO 3260, *Gluconobacter cerinus* IFO 3266, *Gluconobacter oxydans* IFO 3287, and *Acetobacter aceti* subsp. *orleanus* IFO 3259, which were all deposited on Apr. 5, 1954; *Acetobacter aceti* subsp. *xylinum* IFO 13693 deposited on Oct. 22, 1975, and *Acetobacter aceti* subsp. *xylinum* IFO 13773 deposited on Dec. 8, 1977. Strain *Acetobacter* sp. ATCC 15164, which is also an example of a preferred bacterium, was deposited with ATCC. Strain *Gluconobacter oxydans* (formerly known as *G. melanogenus*) N 44-1 as another example of a preferred bacterium is a derivative of the strain IFO 3293 and is described in Sugisawa et al., Agric. Biol. Chem. 54: 1201-1209, 1990.

A microorganism as of the present invention may carry further modifications either on the DNA or protein level (see above), as long as such modification has a direct impact on the yield, production and/or efficiency of the direct production of Vitamin C from substrates like e.g. D-sorbitol or L-sorbose. Such further modifications may for instance affect other genes encoding SMS proteins as described above, in particular genes encoding membrane-bound L-sorbosone dehydrogenases, such as L-sorbosone dehydrogenase SNDHai, or membrane-bound PQQ bound D-sorbitol dehydrogenases. Methods of performing such modifications are known in the art, with some examples further described herein. For the use of SNDHai for direct production of vitamin C as well as the nucleotide and amino acid sequence thereof we refer to WO 2005/017159 which is incorporated herein by reference.

In accordance with a further object of the present invention there is provided the use of a polynucleotide as defined above or a microorganism which is genetically engineered using such polynucleotides in the production of Vitamin C.

The invention also relates to processes for the expression of endogenous genes in a microorganism, to processes for the production of polypeptides as defined above in a microorganism and to processes for the production of microorganisms capable of producing Vitamin C. All these processes may comprise the step of altering a microorganism, wherein "altering" as used herein encompasses the process for "genetically altering" or "altering the composition of the cell culture media and/or methods used for culturing" in such a way that the yield and/or productivity of the fermentation product can be improved compared to the wild-type organism. As used herein, "improved yield of Vitamin C" means an increase of at least 5%, 10%, 25%, 30%, 40%, 50%, 75%, 100%, 200% or even more than 500%, compared to a wild-type microorganism, i.e. a microorganism which is not genetically altered.

The term "genetically engineered" or "genetically altered" means the scientific alteration of the structure of genetic material in a living organism. It involves the production and use of recombinant DNA. More in particular it is used to delineate the genetically engineered or modified organism from the naturally occurring organism. Genetic engineering may be done by a number of techniques known in the art, such as e.g. gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

In accordance with still another aspect of the invention there is provided a process for the production of Vitamin C by direct fermentation.

In particular, the present invention provides a process for the direct production of Vitamin C comprising converting a substrate into Vitamin C. This may for instance be done in a medium comprising a microorganism, which may be a resting or a growing microorganism, preferably a resting microorganism.

Several substrates may be used as a carbon source in a process of the present invention, i.e. a process for direct conversion of a given substrate into Vitamin C such as e.g. mentioned above. Particularly suited carbon sources are those that are easily obtainable from the D-glucose or D-sorbitol metabolization pathway such as, for example, D-glucose, D-sorbitol, L-sorbose, L-sorbosone, 2-keto-L-gulonate, D-gluconate, 2-keto-D-gluconate or 2,5-diketo-gluconate. Preferably, the substrate is selected from for instance D-glucose, D-sorbitol, L-sorbose or L-sorbosone, more preferably from D-glucose, D-sorbitol or L-sorbose, and most preferably from D-sorbitol, L-sorbose or L-sorbosone. The term "substrate" and "production substrate" in connection with the above process using a microorganism is used interchangeably herein.

A medium as used herein for the above process using a microorganism may be any suitable medium for the production of Vitamin C. Typically, the medium is an aqueous medium comprising for instance salts, substrate(s), and a certain pH. The medium in which the substrate is converted into Vitamin C is also referred to as the production medium.

"Fermentation" or "production" or "fermentation process" as used herein may be the use of growing cells using media, conditions and procedures known to the skilled person, or the use of non-growing so-called resting cells, after they have been cultivated by using media, conditions and procedures known to the skilled person, under appropriate conditions for the conversion of suitable substrates into desired products such as Vitamin C. Preferably, resting cells are used for the production of Vitamin C.

The term "direct fermentation", "direct production", "direct conversion" and the like is intended to mean that a microorganism is capable of the conversion of a certain substrate into the specified product by means of one or more biological conversion steps, without the need of any additional chemical conversion step. For instance, the term "direct conversion of D-sorbitol into Vitamin C" is intended to describe a process wherein a microorganism is producing Vitamin C and wherein D-sorbitol is offered as a carbon source without the need of an intermediate chemical conversion step. A single microorganism capable of directly fermenting Vitamin C is preferred. Said microorganism is cultured under conditions which allow such conversion from the substrate as defined above.

In connection with the above process using a microorganism it is understood that the above-mentioned microorganisms also include synonyms or basonyms of such species having the same physiological properties, as defined by the International Code of Nomenclature of Prokaryotes. The nomenclature of the microorganisms as used herein is the one officially accepted (at the filing date of the priority application) by the International Committee on Systematics of Prokaryotes and the Bacteriology and Applied Microbiology Division of the International Union of Microbiological Societies, and published by its official publication vehicle International Journal of Systematic and Evolutionary Microbiology (IJSEM). A particular reference is made to Urbance et al., IJSEM (2001) vol 51:1059-1070, with a corrective notification on IJSEM (2001) vol 51:1231-1233, describing the taxonomically reclassification of *G. oxydans* DSM 4025 as *Ketogulonicigenium vulgare*.

As used herein, resting cells refer to cells of a microorganism which are for instance viable but not actively growing, or which are growing at low specific growth rates, for instance, growth rates that are lower than 0.02 $h^{-1}$, preferably lower than 0.01 $h^{-1}$. Cells which show the above growth rates are said to be in a "resting cell mode".

The process of the present invention as above using a microorganism may be performed in different steps or phases: preferably, the microorganism is cultured in a first step (also referred to as step (a) or growth phase) under conditions which enable growth. This phase is terminated by changing of the conditions such that the growth rate of the microorganism is reduced leading to resting cells, also referred to as step (b), followed by the production of Vitamin C from the substrate using the (b), also referred to as production phase.

Growth and production phase as performed in the above process using a microorganism may be performed in the same vessel, i.e., only one vessel, or in two or more different vessels, with an optional cell separation step between the two phases. The produced Vitamin C can be recovered from the cells by any suitable means. Recovering means for instance that the produced Vitamin C may be separated from the production medium. Optionally, the thus produced Vitamin C may be further processed.

For the purpose of the present invention relating to the above process using a microorganism, the terms "growth phase", "growing step", "growth step" and "growth period" are used interchangeably herein. The same applies for the terms "production phase", "production step", "production period".

One way of performing the above process using a microorganism as of the present invention may be a process wherein the microorganism is grown in a first vessel, the so-called growth vessel, as a source for the resting cells, and at least part of the cells are transferred to a second vessel, the so-called production vessel. The conditions in the production vessel may be such that the cells transferred from the growth vessel become resting cells as defined above. Vitamin C is produced in the second vessel and recovered therefrom.

In connection with the above process using a microorganism, in one aspect, the growing step can be performed in an aqueous medium, i.e. the growth medium, supplemented with appropriate nutrients for growth under aerobic conditions. The cultivation may be conducted, for instance, in batch, fed-batch, semi-continuous or continuous mode. The cultivation period may vary depending on for instance the host, pH, temperature and nutrient medium to be used, and may be for instance about 10 h to about 10 days, preferably about 1 to about 10 days, more preferably about 1 to about 5 days when run in batch or fed-batch mode, depending on the microorganism. If the cells are grown in continuous mode, the residence time may be for instance from about 2 to about 100 h, preferably from about 2 to about 50 h, depending on the microorganism. If the microorganism is selected from bacteria, the cultivation may be conducted for instance at a pH of about 3.0 to about 9.0, preferably about 4.0 to about 9.0, more preferably about 4.0 to about 8.0, even more preferably about 5.0 to about 8.0. If algae or yeast are used, the cultivation may be conducted, for instance, at a pH below about 7.0, preferably below about 6.0, more preferably below about 5.5; and most preferably below about 5.0. A suitable temperature range for carrying out the cultivation using bacteria may be for instance from about 13° C. to about 40° C., preferably from about 18° C. to about 37° C., more preferably from about 13° C. to about 36° C., and most preferably from about 18° C. to about 33° C. If algae or yeast are used, a suitable temperature range for carrying out the cultivation may be for instance from about 15° C. to about 40° C., preferably from about 20° C. to about 45° C., more preferably from about 25° C. to about 40° C., even more preferably from about 25° C. to about 38° C., and most preferably from about 30° C. to about 38° C. The culture medium for growth usually may contain such nutrients as assimilable carbon sources, e.g., glycerol, D-mannitol, D-sorbitol, L-sorbose, erythritol, ribitol, xylitol, arabitol, inositol, dulcitol, D-ribose, D-fructose, D-glucose, sucrose, and ethanol, preferably L-sorbose, D-glucose, D-sorbitol, D-mannitol, glycerol and ethanol; and digestible nitrogen sources such as organic substances, e.g., peptone, yeast extract and amino acids. The media may be with or without urea and/or corn steep liquor and/or baker's yeast. Various inorganic substances may also be used as nitrogen sources, e.g., nitrates and ammonium salts. Furthermore, the growth medium, usually may contain inorganic salts, e.g., magnesium sulfate, manganese sulfate, potassium phosphate, and calcium carbonate. Cells obtained using the procedures described above can then be further incubated at essentially the same modes, temperature and pH conditions as described above, in the presence of substrates such as D-sorbitol, L-sorbose, or D-glucose, in such a way that they convert these substrates directly into Vitamin C. Incubation can be done in a nitrogen-rich medium, containing, for example, organic nitrogen sources, e.g., peptone, yeast extract, baker's yeast, urea, amino acids, and corn steep liquor, or inorganic nitrogen sources, e.g., nitrates and ammonium salts, in which case cells will be able to further grow while producing Vitamin C. Alternatively, incubation can be done in a nitrogen-poor medium, in which case cells will not grow substantially, and will be in a resting cell mode, or biotransformation mode. In all cases, the incubation medium may also contain inorganic salts, e.g., magnesium sulfate, manganese sulfate, potassium phosphate, and calcium chloride.

In connection with the above process using a microorganism, in the growth phase the specific growth rates are for instance at least $0.02\ h^{-1}$. For cells growing in batch, fed-batch or semi-continuous mode, the growth rate depends on for instance the composition of the growth medium, pH, temperature, and the like. In general, the growth rates may be for instance in a range from about 0.05 to about $0.2\ h^{-1}$, preferably from about 0.06 to about $0.15\ h^{-1}$, and most preferably from about 0.07 to about $0.13\ h^{-1}$.

In another aspect of the above process using a microorganism, resting cells may be provided by cultivation of the respective microorganism on agar plates thus serving as growth vessel, using essentially the same conditions, e.g., cultivation period, pH, temperature, nutrient medium as described above, with the addition of agar agar.

In connection with the above process using a microorganism, if the growth and production phase are performed in two separate vessels, then the cells from the growth phase may be harvested or concentrated and transferred to a second vessel, the so-called production vessel. This vessel may contain an aqueous medium supplemented with any applicable production substrate that can be converted to Vitamin C by the cells. Cells from the growth vessel can be harvested or concentrated by any suitable operation, such as for instance centrifugation, membrane crossflow ultrafiltration or microfiltration, filtration, decantation, flocculation. The cells thus obtained may also be transferred to the production vessel in the form of the original broth from the growth vessel, without being harvested, concentrated or washed, i.e. in the form of a cell suspension. In a preferred embodiment, the cells are transferred from the growth vessel to the production vessel in the form of a cell suspension without any washing or isolating step in-between.

Thus, in a preferred embodiment of the above process using a microorganism step (a) and (c) of the process of the present invention as described above are not separated by any washing and/or separation step.

In connection with the above process using a microorganism, if the growth and production phase are performed in the same vessel, cells may be grown under appropriate conditions to the desired cell density followed by a replacement of the growth medium with the production medium containing the production substrate. Such replacement may be, for instance, the feeding of production medium to the vessel at the same time and rate as the withdrawal or harvesting of supernatant from the vessel. To keep the resting cells in the vessel, operations for cell recycling or retention may be used, such as for instance cell recycling steps. Such recycling steps, for instance, include but are not limited to methods using centrifuges, filters, membrane crossflow microfiltration of ultrafiltration steps, membrane reactors, flocculation, or cell immobilization in appropriate porous, non-porous or polymeric matrixes. After a transition phase, the vessel is brought to process conditions under which the cells are in a resting cell mode as defined above, and the production substrate is efficiently converted into Vitamin C.

The aqueous medium in the production vessel as used for the production step in connection with the above process using a microorganism, hereinafter called production medium, may contain only the production substrate(s) to be converted into Vitamin C, or may contain for instance additional inorganic salts, e.g., sodium chloride, calcium chloride, magnesium sulfate, manganese sulfate, potassium phosphate, calcium phosphate, and calcium carbonate. The production medium may also contain digestible nitrogen sources such as for instance organic substances, e.g., peptone, yeast extract, urea, amino acids, and corn steep liquor, and inorganic substances, e.g. ammonia, ammonium sulfate, and sodium nitrate, at such concentrations that the cells are kept in a resting cell mode as defined above. The medium may be with or without urea and/or corn steep liquor and/or baker's yeast. The production step may be conducted for instance in batch, fed-batch, semi-continuous or continuous mode. In case of fed-batch, semi-continuous or continuous mode, both cells from the growth vessel and production medium can be fed continuously or intermittently to the production vessel at appropriate feed rates. Alternatively, only production medium may be fed continuously or intermittently to the production vessel, while the cells coming from the growth vessel are transferred at once to the production vessel. The cells coming from the growth vessel may be used as a cell suspension within the production vessel or may be used as for instance flocculated or immobilized cells in any solid phase such as porous or polymeric matrixes. The production period, defined as the period elapsed between the entrance of the substrate into the production vessel and the harvest of the supernatant containing Vitamin C, the so-called harvest stream, can vary depending for instance on the kind and concentration of cells, pH, temperature and nutrient medium to be used, and is preferably about 2 to about 100 h. The pH and temperature can be different from the pH and temperature of the growth step, but is essentially the same as for the growth step.

In a preferred embodiment of the above process using a microorganism, the production step is conducted in continuous mode, meaning that a first feed stream containing the cells from the growth vessel and a second feed stream containing the substrate is fed continuously or intermittently to the production vessel. The first stream may either contain only the cells isolated/separated from the growth medium or a cell suspension, coming directly from the growth step, i.e. cells suspended in growth medium, without any intermediate step of cell separation, washing and/or isolating. The second feed stream as herein defined may include all other feed streams necessary for the operation of the production step, e.g. the production medium comprising the substrate in the form of one or several different streams, water for dilution, and base for pH control.

In connection with the above process using a microorganism, when both streams are fed continuously, the ratio of the feed rate of the first stream to feed rate of the second stream may vary between about 0.01 and about 10, preferably between about 0.01 and about 5, most preferably between about 0.02 and about 2. This ratio is dependent on the concentration of cells and substrate in the first and second stream, respectively.

Another way of performing the process as above using a microorganism of the present invention may be a process using a certain cell density of resting cells in the production vessel. The cell density is measured as absorbance units (optical density) at 600 nm by methods known to the skilled person. In a preferred embodiment, the cell density in the production step is at least about 10, more preferably between about 10 and about 200, even more preferably between about 15 and about 200, even more preferably between about 15 to about 120, and most preferably between about 20 and about 120.

In connection with the above process using a microorganism, in order to keep the cells in the production vessel at the desired cell density during the production phase as performed, for instance, in continuous or semi-continuous mode, any means known in the art may be used, such as for instance cell recycling by centrifugation, filtration, membrane crossflow ultrafiltration of microfiltration, decantation, flocculation, cell retention in the vessel by membrane devices or cell immobilization. Further, in case the production step is performed in continuous or semi-continuous mode and cells are continuously or intermittently fed from the growth vessel, the cell density in the production vessel may be kept at a constant level by, for instance, harvesting an amount of cells from the production vessel corresponding to the amount of cells being fed from the growth vessel.

In connection with the above process using a microorganism, the produced Vitamin C contained in the so-called harvest stream is recovered/harvested from the production vessel. The harvest stream may include, for instance, cell-free or cell-containing aqueous solution coming from the production vessel, which contains Vitamin C as a result of the conversion of production substrate by the resting cells in the production vessel. Cells still present in the harvest stream may be separated from the Vitamin C by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

In a further aspect, the process of the present invention may be combined with further steps of separation and/or purification of the produced Vitamin C from other components contained in the harvest stream, i.e., so-called downstream processing steps. These steps may include any means known to a skilled person, such as, for instance, concentration, crystallization, precipitation, adsorption, ion exchange, electrodialysis, bipolar membrane electrodialysis and/or reverse osmosis. Vitamin C may be further purified as the free acid form or any of its known salt forms by means of operations such as for instance treatment with activated carbon, ion exchange, adsorption and elution, concentration, crystallization, filtration and drying. Specifically, a first separation of Vitamin C from other components in the harvest stream might be performed by any suitable combination or repetition of, for instance, the following methods: two- or three-compartment electrodialysis, bipolar membrane electrodialysis, reverse osmosis or adsorption on, for instance, ion exchange resins or non-ionic resins. If the resulting form of Vitamin C is a salt of L-ascorbic acid, conversion of the salt form into the free acid form may be performed by for instance bipolar membrane electrodialysis, ion exchange, simulated moving bed chromatographic techniques, and the like. Combination of the mentioned steps, e.g., electrodialysis and bipolar membrane electrodialysis into one step might be also used as well as combination of the mentioned steps e.g. several steps of ion exchange by using simulated moving bed chromatographic methods. Any of these procedures alone or in combination constitute a convenient means for isolating and purifying the product, i.e. Vitamin C. The product thus obtained may further be isolated in a manner such as, e.g. by concentration, crystallization, precipitation, washing and drying of the crystals and/or further purified by, for instance, treatment with activated carbon, ion exchange and/or re-crystallization.

In a preferred embodiment, Vitamin C is purified from the harvest stream by a series of downstream processing steps as described above without having to be transferred to a non-aqueous solution at any time of this processing, i.e. all steps are performed in an aqueous environment. Such preferred downstream processing procedure may include for instance the concentration of the harvest stream coming from the production vessel by means of two- or three-compartment electrodialysis, conversion of Vitamin C in its salt form present in the concentrated solution into its acid form by means of bipolar membrane electrodialysis and/or ion exchange, purification by methods such as for instance treatment with activated carbon, ion exchange or non-ionic resins, followed by a further concentration step and crystallization. These crystals can be separated, washed and dried. If necessary, the crystals may be again re-solubilized in water, treated with activated carbon and/or ion exchange resins and recrystallized. These crystals can then be separated, washed and dried.

Advantageous embodiments of the invention become evident from the dependent claims. These and other aspects and embodiments of the present invention should be apparent to those skilled in the art from the teachings herein.

The sequence of the gene comprising a nucleotide sequence according to SEQ ID NO:1 encoding a SMS 05 protein was determined by sequencing a genomic clone obtained from *Gluconobacter oxydans* DSM 17078.

The invention also relates to a polynucleotide encoding at least a biologically active fragment or derivative of a SMS 05 polypeptide as shown in SEQ ID NO:2.

As used herein, "biologically active fragment or derivative" means a polypeptide which retains essentially the same biological function or activity as the polypeptide shown in SEQ ID NO:2. Examples of biological activity may for instance be enzymatic activity, signaling activity or antibody reactivity. The term "same biological function" or "functional equivalent" as used herein means that the protein has essentially the same biological activity, e.g. enzymatic, signaling or antibody reactivity, as a polypeptide shown in SEQ ID NO:2.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides could be part of a composition and still be isolated in that such vector or composition is not part of its natural environment.

An isolated polynucleotide or nucleic acid as used herein may be a DNA or RNA that is not immediately contiguous with both of the coding sequences with which it is immediately contiguous (one on the 5'-end and one on the 3'-end) in the naturally occurring genome of the organism from which it is derived. Thus, in one embodiment, a nucleic acid includes some or all of the 5'-non-coding (e.g., promoter) sequences that are immediately contiguous to the coding sequence. The term "isolated polynucleotide" therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "is isolated nucleic acid fragment" is a nucleic acid fragment that is not naturally occurring as a fragment and would not be found in the natural state.

As used herein, the terms "polynucleotide", "gene" and "recombinant gene" refer to nucleic acid molecules which may be isolated from chromosomal DNA, which include an open reading frame encoding a protein, e.g. *G. oxydans* DSM 17078 SMS proteins. A polynucleotide may include a polynucleotide sequence as shown in SEQ ID NO:1 or fragments thereof and regions upstream and downstream of the gene sequences which may include, for example, promoter regions, regulator regions and terminator regions important for the appropriate expression and stabilization of the polypeptide derived thereof.

A gene may include coding sequences, non-coding sequences such as for instance untranslated sequences located at the 3'- and 5'-ends of the coding region of a gene, and regulatory sequences. Moreover, a gene refers to an isolated nucleic acid molecule as defined herein. It is furthermore appreciated by the skilled person that DNA sequence polymorphisms that lead to changes in the amino acid sequences of SMS proteins may exist within a population, e.g., the *Gluconobacter oxydans* population. Such genetic polymorphism in the SMS 05 gene may exist among individuals within a population due to natural variation or in cells from different populations. Such natural variations can typically result in 1-5% variance in the nucleotide sequence of the SMS 05 gene. Any and all such nucleotide variations and the resulting amino acid polymorphism in SMS 05 are the result of natural variation and that do not alter the functional activity of SMS proteins are intended to be within the scope of the invention.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule may be single-stranded or double-stranded, but preferably is double-stranded DNA. The nucleic acid may be synthesized using oligonucleotide analogs or derivatives (e.g., inosine or phosphorothioate nucleotides). Such oligonucleotides may be used, for example, to prepare nucleic acids that have altered base-pairing abilities or increased resistance to nucleases.

The sequence information as provided herein should not be so narrowly construed as to require inclusion of erroneously identified bases. The specific sequences disclosed herein may be readily used to isolate the complete gene from a recombinant or non-recombinant microorganism capable of converting a given carbon source directly into Vitamin C, in particular *Gluconobacter oxydans*, preferably *Gluconobacter oxydans* DSM 17078 which in turn may easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence may be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

A nucleic acid molecule according to the invention may comprise only a portion or a fragment of the nucleic acid sequence provided by the present invention, such as for instance the sequence shown in SEQ ID NO:1, for example a fragment which may be used as a probe or primer such as for instance SEQ ID NO:3 or SEQ ID NO:4 or a fragment encoding a portion of a protein according to the invention. The nucleotide sequence determined from the cloning of the SMS 05 gene allows for the generation of probes and primers designed for use in identifying and/or cloning other SMS 05 family members, as well as SMS 05 homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence shown in SEQ ID NO:1 or a fragment or derivative thereof.

A nucleic acid molecule encompassing all or a portion of the nucleic acid sequence of SEQ ID NO:1 may be also isolated by the polymerase chain reaction (PCR) using synthetic oligonucleotide primers designed based upon the sequence information contained herein.

A nucleic acid of the invention may be amplified using cDNA, mRNA or alternatively, genomic DNA, as a template and appropriate oligonucleotide primers according to standard PCR amplification techniques. The nucleic acid thus amplified may be cloned into an appropriate vector and characterized by DNA sequence analysis.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides, may be used as hybridization probes or polymerase chain reaction (PCR) primers. Uses of the nucleic acid molecules of the present invention that do not encode a polypeptide having a SMS 05 activity include, inter alia, (1) isolating the gene encoding the protein of the present invention, or allelic variants thereof from a cDNA library, e.g., from other organisms than *Gluconobacter oxydans* and (2) Northern blot analysis for detecting expression of mRNA of said protein in specific cells or (3) use in enhancing and/or improving the function or activity of homologous SMS 05 genes in said other organisms.

Probes based on the nucleotide sequences provided herein may be used to detect transcripts or genomic sequences encoding the same or homologous proteins for instance in other organisms. Nucleic acid molecules corresponding to natural variants and non-*G. oxydans* homologues of the *G. oxydans* SMS 05 DNA of the invention which are also embraced by the present invention may be isolated based on their homology to the *G. oxydans* SMS 05 nucleic acid disclosed herein using the *G. oxydans* DNA, or a portion thereof, as a hybridization probe according to standard hybridization techniques, preferably under highly stringent hybridization conditions.

In preferred embodiments, the probe further comprises a label group attached thereto, e.g., the label group can be a radioisotope, a fluorescent compound, an enzyme, or an enzyme cofactor.

Homologous gene sequences may be isolated, for example, by performing PCR using two degenerate oligonucleotide primer pools designed on the basis of nucleotide sequences as taught herein.

The template for the reaction may be cDNA obtained by reverse transcription of mRNA prepared from strains known or suspected to express a polynucleotide according to the invention. The PCR product may be subcloned and sequenced to ensure that the amplified sequences represent the sequences of a new nucleic acid sequence as described herein, or a functional equivalent thereof.

The PCR fragment may then be used to isolate a full length cDNA clone by a variety of known methods. For example, the amplified fragment may be labeled and used to screen a bacteriophage or cosmid cDNA library. Alternatively, the labeled fragment may be used to screen a genomic library.

PCR technology can also be used to isolate full-length cDNA sequences from other organisms. For example, RNA may be isolated, following standard procedures, from an appropriate cellular or tissue source. A reverse transcription reaction may be performed on the RNA using an oligonucleotide primer specific for the most 5'-end of the amplified fragment for the priming of first strand synthesis.

The resulting RNA/DNA hybrid may then be "tailed" (e.g., with guanines) using a standard terminal transferase reaction, the hybrid may be digested with RNaseH, and second strand synthesis may then be primed (e.g., with a poly-C primer). Thus, cDNA sequences upstream of the amplified fragment may easily be isolated. For a review of useful cloning strategies, see e.g., Sambrook et al., supra; and Ausubel et al., supra.

Also, nucleic acids encoding other SMS 05 family members, which thus have a nucleotide sequence that differs from a nucleotide sequence according to SEQ ID NO:1, are within the scope of the invention. Moreover, nucleic acids encoding SMS 05 proteins from different species which thus may have a nucleotide sequence which differs from a nucleotide sequence shown in SEQ ID NO:1 are within the scope of the invention.

The invention also relates to an isolated polynucleotide hybridisable under stringent conditions, preferably under highly stringent conditions, to a polynucleotide as of the present invention, such as for instance a polynucleotide shown in SEQ ID NO:1. Advantageously, such polynucleotide may be obtained from a microorganism capable of converting a given carbon source directly into Vitamin C, in particular *Gluconobacter oxydans*, preferably *Gluconobacter oxydans* DSM 17078.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% homologous to each other typically remain hybridized to each other.

In one embodiment, a nucleic acid of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence shown in SEQ ID NO:1 or the complement thereof.

A preferred, non-limiting example of stringent hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 h to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Preferably, an isolated nucleic acid molecule of the invention that hybridizes under preferably highly stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *G. oxydans* SMS 05 protein.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.). Of course, a polynucleotide which hybridizes only to a poly (A) sequence (such as the 3'-terminal poly (A) tract of mRNAs), or to a complementary stretch of T (or U) residues, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, genomic DNA or cDNA libraries constructed from other organisms, e.g. microorganisms capable of converting a given carbon source directly into Vitamin C, in particular other *Gluconobacter* species may be screened.

For example, *Gluconobacter* strains may be screened for homologous polynucleotides by Southern and/or Northern blot analysis. Upon detection of transcripts homologous to polynucleotides according to the invention, DNA libraries may be constructed from RNA isolated from the appropriate strain, utilizing standard techniques well known to those of skill in the art. Alternatively, a total genomic DNA library may be screened using a probe hybridisable to a polynucleotide according to the invention.

A nucleic acid molecule of the present invention, such as for instance a nucleic acid molecule shown in SEQ ID NO:1 or a fragment or derivative thereof, may be isolated using standard molecular biology techniques and the sequence information provided herein. For example, using all or portion of the nucleic acid sequence shown in SEQ ID NO:1 as a hybridization probe, nucleic acid molecules according to the invention may be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to nucleotide sequences according to the invention may be prepared by standard synthetic techniques, e.g., using an automated DNA synthesizer.

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). Preferably, the two sequences are the same length.

The skilled person will be aware of the fact that several different computer programs are available to determine the homology between two sequences. For instance, a comparison of sequences and determination of percent identity between two sequences may be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at URL: accelrys[dot]com), using either a Blossom 62 matrix or a PAM250 matrix, and a gap weight of 16, 14, 12, 10, 8, 6 or 4 and a length weight of 1, 2, 3, 4, 5 or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at URL: accelrys[dot]com), using a NWSgapdna.CMP matrix and a gap weight of 40, 50, 60, 70 or 80 and a length weight of 1, 2, 3, 4, 5 or 6. In another embodiment, the percent identity between two amino acid or nucleotide sequences is determined using the algorithm of E. Meyers and W. Miller (CABIOS, 4: 11-17 (1989) which has been incorporated into the ALIGN program (version 2.0) (available at URL: vega[dot]igh[dot]cnrs[dot]fr/bin[slash]align-guess[dot]cgi) using a PAM120 weight residue table, a gap length penalty of 12 and a gap penalty of 4.

The nucleic acid and protein sequences of the present invention may further be used as a "query sequence" to perform a search against public databases to, for example, identify other family members or related sequences. Such searches may be performed using the BLASTN and BLASTX programs (version 2.0) of Altschul, et al. (1990) J. Mol. Biol. 215:403-10. BLAST nucleotide searches may be performed with the BLASTN program, score=100, word length=12 to obtain nucleotide sequences homologous to the nucleic acid molecules of the present invention. BLAST protein searches may be performed with the BLASTX program, score=50, word length=3 to obtain amino acid sequences homologous to the protein molecules of the present invention. To obtain gapped alignments for comparison purposes, Gapped BLAST may be utilized as described in Altschul et al., (1997) Nucleic Acids Res. 25 (17): 3389-3402. When utilizing BLAST and Gapped BLAST programs, the default parameters of the respective programs (e.g., BLASTX and BLASTN) may be used. See URL www[dot]ncbi[dot]nlm[dot]nih[dot]gov.

In another preferred embodiment, an isolated nucleic acid molecule of the invention comprises a nucleic acid molecule which is the complement of a nucleotide sequence as of the present invention, such as for instance the sequence shown in SEQ ID NO:1. A nucleic acid molecule, which is complementary to a nucleotide sequence disclosed herein, is one that is sufficiently complementary to a nucleotide sequence shown in SEQ ID NO:1 such that it may hybridize to said nucleotide sequence thereby forming a stable duplex.

In a further preferred embodiment, a nucleic acid of the invention as shown in SEQ ID NO:1 or the complement thereof contains at least one mutation leading to a gene product with modified function/activity. The at least one mutation may be introduced by methods described herein. In one aspect, the at least one mutation leads to a SMS 05 protein whose function compared to the wild type counterpart is completely or partially destroyed. Methods for introducing such mutations are well known in the art.

The term "reduction" of activity as used herein encompasses decreasing activity of one or more polypeptides in the producing organism, which in turn are encoded by the corresponding polynucleotides described herein. There are a number of methods available in the art to accomplish reduction of activity of a given protein, in this case the SMS 05 protein. In general, the specific activity of a protein may be decreased or the copy number of the protein may be decreased.

To facilitate such a decrease, the copy number of the genes corresponding to the polynucleotides described herein may be decreased, such as for instance by underexpression or disruption of a gene. A gene is said to be "underexpressed" if the level of transcription of said gene is reduced in comparison to the wild type gene. This may be measured by for instance Northern blot analysis quantifying the amount of mRNA as an indication for gene expression. As used herein, a gene is underexpressed if the amount of generated mRNA is decreased by at least 1%, 2%, 5% 10%, 25%, 50%, 75%, 100%, 200% or even more than 500%, compared to the amount of mRNA generated from a wild-type gene. Alternatively, a weak promoter may be used to direct the expression of the polynucleotide. In another embodiment, the promoter, regulatory region and/or the ribosome binding site upstream of the gene can be altered to achieve the down-expression. The expression may also be reduced by decreasing the relative half-life of the messenger RNA. In another embodiment, the activity of the polypeptide itself may be decreased by employing one or more mutations in the polypeptide amino acid sequence, which decrease the activity. For example, altering the affinity of the polypeptide for its corresponding substrate may result in reduced activity. Likewise, the relative half-life of the polypeptide may be decreased. In either scenario, that being reduced gene expression or reduced activity, the reduction may be achieved by altering the composition of the cell culture media and/or methods used for culturing. "Reduced expression" or "reduced activity" as used herein means a decrease of at least 5%, 10%, 25%, 50%, 75%, 100%, 200% or even more than 500%, compared to a wild-type protein, polynucleotide, gene; or the activity and/or the concentration of the protein present before the polynucleotides or polypeptides are reduced. The activity of the SMS 05 protein may also be reduced by contacting the protein with a specific or general inhibitor of its activity. The terms "reduced activity", "decreased or abolished activity" are used interchangeably herein.

Another aspect of the invention pertains to vectors, containing a nucleic acid encoding a protein according to the invention or a functional equivalent or portion thereof. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome.

The recombinant vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., attenuator). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention may be introduced into host cells to thereby produce proteins or peptides, encoded by nucleic acids as described herein, including, but not limited to, mutant proteins, fragments thereof, variants or functional equivalents thereof, and fusion proteins, encoded by a nucleic acid as described herein, e.g., SMS 05 proteins, mutant forms of SMS 05 proteins, fusion proteins and the like.

The recombinant expression vectors of the invention may be designed for expression of SMS 05 proteins in a suitable microorganism. For example, a protein according to the invention may be expressed in bacterial cells such as strains belonging to the genera *Gluconobacter, Gluconacetobacter* or *Acetobacter*. Expression vectors useful in the present invention include chromosomal-, episomal- and virus-derived vectors e.g., vectors derived from bacterial plasmids, bacteriophage, and vectors derived from combinations thereof, such as those derived from plasmid and bacteriophage genetic elements, such as cosmids and phagemids.

The DNA insert may be operatively linked to an appropriate promoter, which may be either a constitutive or inducible promoter. The skilled person will know how to select suitable promoters. The expression constructs may contain sites for transcription initiation, termination, and, in the transcribed region, a ribosome binding site for translation. The coding portion of the mature transcripts expressed by the constructs may preferably include an initiation codon at the beginning and a termination codon appropriately positioned at the end of the polypeptide to be translated.

Vector DNA may be introduced into suitable host cells via conventional transformation or transfection techniques. As used herein, the terms "transformation", "transconjugation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipid mediated transfection or electroporation. Suitable methods for transforming or transfecting host cells may be found in Sambrook, et al. (supra), Davis et al., Basic Methods in Molecular Biology (1986) and other laboratory manuals.

In order to identify and select cells which have integrated the foreign DNA into their genome, a gene that encodes a selectable marker (e.g., resistance to antibiotics) is generally introduced into the host cells along with the gene of interest. Preferred selectable markers include those that confer resistance to drugs, such as kanamycin, tetracycline, ampicillin and streptomycin. A nucleic acid encoding a selectable marker is preferably introduced into a host cell on the same vector as that encoding a protein according to the invention or can be introduced on a separate vector such as, for example, a suicide vector, which cannot replicate in the host cells. Cells stably transfected with the introduced nucleic acid can be identified by drug selection (e.g., cells that have incorporated the selectable marker gene will survive, while the other cells die).

The invention provides also an isolated polypeptide having the amino acid sequence shown in SEQ ID NO:2 or an amino acid sequence obtainable by expressing a polynucleotide of the present invention, such as for instance a polynucleotide sequence shown in SEQ ID NO:1 in an appropriate host.

Polypeptides according to the invention may contain only conservative substitutions of one or more amino acids in the amino acid sequence represented by SEQ ID NO:2 or substitutions, insertions or deletions of non-essential amino acids. Accordingly, a non-essential amino acid is a residue that may be altered in the amino acid sequences shown in SEQ ID NO:2 without substantially altering the biological function. For example, amino acid residues that are conserved among the proteins of the present invention, are predicted to be particularly unamenable to alteration. Furthermore, amino acids conserved among the proteins according to the present invention and other SMS 05 proteins are not likely to be amenable to alteration.

The term "conservative substitution" is intended to mean that a substitution in which the amino acid residue is replaced with an amino acid residue having a similar side chain. These families are known in the art and include amino acids with basic side chains (e.g., lysine, arginine and histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As mentioned above, the polynucleotides of the invention may be utilized in the genetic engineering of a suitable host cell to make it better and more efficient in the fermentation, for example in a direct fermentation process for Vitamin C.

According to the invention a genetically engineered/recombinantly produced host cell (also referred to as recombinant cell or transformed cell) carrying such a modified polynucleotide wherein the function of the linked protein is significantly modified in comparison to a wild-type cell such that the yield, production and/or efficiency of production of one or more fermentation products such as Vitamin C is improved. The host cell may be selected from a microorganism capable of directly producing one or more fermentation products such as for instance Vitamin C from a given carbon source, in particular *Gluconobacter oxydans*, preferably *G. oxydans* DSM 17078.

A "transformed cell" or "recombinant cell" is a cell into which (or into an ancestor of which) has been introduced, by means of recombinant DNA techniques, a nucleic acid according to the invention, or wherein the activity of the SMS 05 protein has been decreased or abolished. Suitable host cells include cells of microorganisms capable of producing a given fermentation product, e.g., converting a given carbon source directly into Vitamin C. In particular, these include strains from the genera *Pseudomonas, Pantoea, Escherichia, Corynebacterium, Ketogulonicigenium* and acetic acid bacteria like e.g., *Gluconobacter, Acetobacter* or *Gluconacetobacter*, preferably *Acetobacter* sp., *Acetobacter aceti, Gluconobacter frateurii, Gluconobacter cerinus, Gluconobacter thailandicus, Gluconobacter oxydans*, more preferably *G. oxydans*, most preferably *G. oxydans* DSM 17078.

To improve the Vitamin C production of a certain recombinant host cell, SMS 05 gene expression may be inhibited in that organism for instance by targeting nucleotide sequences complementary to the regulatory region of a SMS 05 nucleotide sequence (e.g., a SMS 05 promoter and/or enhancers) to form triple helical structures that prevent transcription of a SMS 05 gene in target cells. See generally, Helene, C. (1991) AnticancerDrugDes. 6 (6): 569-84; Helene, C. et al. (1992) Ann. N.Y. Acad. Sci. 660: 27-36; and Maher, L. J. (1992) Bioassays 14 (12): 807-15.

Inhibition or prevention of gene expression may also be achieved by modifying the SMS 05 gene, e.g., by introducing one or more mutations into the SMS 05 gene wherein said modification leads to a SMS 05 protein with a function which is significantly decreased in comparison to the wild-type protein.

Therefore, in one other embodiment, the polynucleotide carrying the at least one mutation is derived from a polynucleotide as represented by SEQ ID NO:1 or equivalents thereof.

A mutation as used herein may be any mutation leading to a less functional or unstable polypeptide, e.g. less functional or unstable SMS 05 gene products. This may include for instance an alteration in the genome of a microorganism, which interferes with the synthesis of SMS 05 or leads to the expression of a SMS 05 protein with an altered amino acid sequence whose function compared with the wild type counterpart having a non-altered amino acid sequence is completely or partially destroyed. The interference may occur at the transcriptional, translational or post-translational level.

The alteration in the genome of the microorganism may be obtained e.g. by replacing through a single or double crossover recombination a wild type DNA sequence by a DNA sequence containing the alteration. For convenient selection of transformants of the microorganism with the alteration in its genome the alteration may, e.g. be a DNA sequence encoding an antibiotic resistance marker or a gene complementing a possible auxotrophy of the microorganism. Mutations include, but are not limited to, deletion-insertion mutations. An example of such an alteration includes a gene disruption, i.e. a perturbation of a gene such that the product that is normally produced from this gene is not produced in a functional form. This could be due to a complete deletion, a deletion and insertion of a selective marker, an insertion of a selective marker, a frameshift mutation, an in-frame deletion, or a point mutation that leads to premature termination. In some of these cases the entire mRNA for the gene is absent, in others the amount of mRNA produced varies. In all cases the polypeptide encoded by said gene is not produced in a functional form, either absent or in a mutated form, such as e.g. a protein having reduced activity as defined herein.

An alteration in the genome of the microorganism leading to a less or non-functional polypeptide may also be obtained by randomly mutagenizing the genome of the microorganism using e.g. chemical mutagens, radiation or transposons and selecting or screening for mutants which are better or more efficient producers of one or more fermentation products. Standard methods for screening and selection are known to the skilled person.

In a specific embodiment, it is desired to knockout the SMS 05 gene of the present invention, i.e., wherein its gene expression is artificially suppressed in order to improve the yield, productivity, and/or efficiency of production of the fermentation product when introduced into a suitable host cell. Methods of providing knockouts as well as microorganisms carrying such suppressed genes are well known in the art. The suppression of the endogenous SMS 05 gene may be induced by deleting at least a part of the gene or the regulatory region thereof. As used herein, "suppression of the gene expression" includes complete and partial suppression, as well as suppression under specific conditions and also suppression of the expression of either one of the two alleles.

In order to create a knockout microorganism in which the expression of the SMS 05 gene is artificially suppressed, first the SMS 05 gene may be cloned and then a vector for homologous recombination may be constructed by using the gene to inactivate the endogenous SMS 05 gene in the target microorganism. The vector for homologous recombination then contains a nucleic acid sequence designed to inactivate the endogenous SMS 05 gene in the target microorganism. Such a nucleic acid may be for instance a nucleic acid sequence of the SMS 05 gene or the regulatory region thereof, such as the existing flanking region of the gene to be inactivated (in cis), or existing separately (in trans), containing at least a partial deletion, or alternatively it may be a nucleic acid sequence of the SMS 05 gene or the regulatory region thereof containing other genes. A gene which can also function as a marker is preferably selected as the gene to be inserted into the SMS 05 gene or the regulatory region thereof. The insert genes to be used include for instance drug-resistance genes as defined above. There is no particular limitation on the position where the genes may be inserted in the SMS 05 gene, as long as the insertion at that position results in the suppression of the expression of the endogenous SMS 05 gene in the target. To avoid polar effects of the insertion, in-frame silent deletions can be introduced by using, for example, the sacB system or long-flanking homology PCR. These techniques are well known to the person skilled in the art.

The aforementioned mutagenesis strategies for SMS 05 proteins may result in increased yields of a desired compound in particular Vitamin C. This list is not meant to be limiting; variations on these mutagenesis strategies will be readily apparent to one of ordinary skill in the art. By these mechanisms, the nucleic acid and protein molecules of the invention may be utilized to generate microorganisms such as *Gluconobacter oxydans* or related strains of bacteria expressing mutated SMS 05 nucleic acid and protein molecules such that the yield, productivity, and/or efficiency of production of a desired compound such as Vitamin C is improved.

In connection with the above process using a microorganism, in one aspect, the process of the present invention leads to yields of Vitamin C which are at least about more than 5.7 g/l, such as 10 g/l, 20 g/l, 50 g/l, 100 g/l, 200 g/l, 300 g/l, 400 g/l or more than 600 g/l. In one embodiment, the yield of Vitamin C produced by the process of the present invention is in the range of from about more than 5.7 to about 600 g/l. The yield of Vitamin C refers to the concentration of Vitamin C in the harvest stream coming directly out of the production vessel, i.e. the cell-free supernatant comprising the Vitamin C.

In one aspect of the invention, microorganisms (in particular from the genera of *Gluconobacter, Gluconacetobacter* and *Acetobacter*) are provided that are able to directly produce Vitamin C from a suitable carbon source like D-sorbitol and/or L-sorbose. When measured for instance in a resting cell method after an incubation period of 20 hours, these organisms were found to be able to produce Vitamin C directly from D-sorbitol or L-sorbose, even up to a level of 280 mg/l and 670 mg/l respectively. In another aspect of the invention, a microorganism is provided capable of directly producing Vitamin C in quantities of 300 mg/l when starting from D-sorbitol or more or 800 mg/l or more when starting from L-sorbose, respectively when for instance measured in a resting cell method after an incubation period of 20 hours. Such may be achieved by decreasing or abolishing the activity of a SMS polypeptide, preferably a SMS 05 polypeptide. The yield of Vitamin C produced from D-sorbitol may even be as high as 400, 600, 1000 mg/l or even exceed 1.5, 2, 4, 10, 20, 50 μl. The yield of Vitamin C produced from L-sorbose may even be as high as 1000 mg/l or even exceed 1.5, 2, 4, 10, 20, 50 g/l. Preferably, these amounts of Vitamin C can be achieved when measured by resting cell method after an incubation period of 20 hours.

As used herein, measurement in a "resting cell method" comprises (i) growing the cells by means of any method well know to the person skilled in the art, (ii) harvesting the cells from the growth broth, and (iii) incubating the harvested cells in a medium containing the substrate which is to be converted into the desired product, e.g. Vitamin C, under conditions where the cells do not grow any longer, i.e. there is no increase in the amount of biomass during this so-called conversion step.

The recombinant microorganism carrying e.g. a modified SMS 05 gene and which is able to produce the fermentation product in significantly higher yield, productivity, and/or efficiency may be cultured in an aqueous medium supplemented with appropriate nutrients under aerobic conditions as described above.

The nucleic acid molecules, polypeptides, vectors, primers, and recombinant microorganisms described herein may be used in one or more of the following methods: identification of *Gluconobacter oxydans* and related organisms; mapping of genomes of organisms related to *Gluconobacter oxydans*; identification and localization of *Gluconobacter oxydans* sequences of interest; evolutionary studies; determination of SMS 05 protein regions required for function; modulation of a SMS 05 protein activity or function; modulation of the activity of a SMS pathway; and modulation of cellular production of a desired compound, such as Vitamin C.

The invention provides methods for screening molecules which modulate the activity of a SMS 05 protein, either by interacting with the protein itself or a substrate or binding partner of the SMS 05 protein, or by modulating the transcription or translation of a SMS 05 nucleic acid molecule of the invention. In such methods, a microorganism expressing one or more SMS 05 proteins of the invention is contacted with one or more test compounds, and the effect of each test compound on the activity or level of expression of the SMS 05 protein is assessed.

The biological, enzymatic or other activity of SMS proteins can be measured by methods well known to a skilled person, such as, for example, by incubating a cell fraction containing the SMS protein in the presence of its substrate, electron acceptor(s) or donor(s) including phenazine methosulfate (PMS), dichlorophenol-indophenol (DCIP), NAD, NADH, NADP, NADPH, which consumption can be directly or indirectly measured by photometric, colorimetric or fluorimetric methods, and other inorganic components which might be relevant for the development of the activity. Thus, for example, the activity of membrane-bound D-sorbitol dehydrogenase can be measured in an assay where membrane fractions containing this enzyme are incubated in the presence of phosphate buffer at pH 6, D-sorbitol and the artificial electron acceptors DCIP and PMS. The rate of consumption of DCIP can be measured at 600 nm, and is directly proportional to the D-sorbitol dehydrogenase activity present in the membrane fraction.

It may be evident from the above description that the fermentation product of the methods according to the invention may not be limited to Vitamin C alone. The "desired compound" or "fermentation product" as used herein may be any natural product of *Gluconobacter oxydans*, which includes the final products and intermediates of biosynthesis pathways, such as for example L-sorbose, L-sorbosone, D-gluconate, 2-keto-D-gluconate, 5-keto-D-gluconate, 2,5-diketo-D-gluconate and 2-keto-L-gulonate (2-KGA), in particular the biosynthetic generation of Vitamin C.

Thus, the present invention is directed to the use of a polynucleotide, polypeptide, vector, primer and recombinant microorganism as described herein in the production of Vitamin C, i.e., the direct conversion of a carbon source into Vitamin C. In a preferred embodiment, a modified polynucleotide, polypeptide, vector and recombinant microorganism as described herein is used for improving the yield, productivity, and/or efficiency of the production of Vitamin C.

The terms "production" or "productivity" are art-recognized and include the concentration of the fermentation product (for example, Vitamin C) formed within a given time and a given fermentation volume (e.g., kg product per hour per liter). The term "efficiency of production" includes the time required for a particular level of production to be achieved (for example, how long it takes for the cell to attain a particular rate of output of a fermentation product). The term "yield" is art-recognized and includes the efficiency of the conversion of the carbon source into the product (i.e., Vitamin C). This is generally written as, for example, kg product per kg carbon source. By "increasing the yield and/or production/productivity" of the compound it is meant that the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound. The language "transport" or "import" is art-recognized and includes the facilitated movement of one or more molecules across a cellular membrane through which the molecule would otherwise either be unable to pass or be passed inefficiently.

Vitamin C as used herein may be any chemical form of L-ascorbic acid found in aqueous solutions, such as for instance undissociated, in its free acid form or dissociated as an anion. The solubilized salt form of L-ascorbic acid may be characterized as the anion in the presence of any kind of cations usually found in fermentation supernatants, such as for instance potassium, sodium, ammonium, or calcium. Also included may be isolated crystals of the free acid form of L-ascorbic acid. On the other hand, isolated crystals of a salt form of L-ascorbic acid are called by their corresponding salt name, i.e. sodium ascorbate, potassium ascorbate, calcium ascorbate and the like.

In one preferred embodiment, the present invention is related to a process for the production of Vitamin C wherein a nucleotide according to the invention or a modified polynucleotide sequence as described above is introduced into a suitable microorganism, the recombinant microorganism is cultured under conditions that allow the production of Vitamin C in high productivity, yield, and/or efficiency, the produced fermentation product is isolated from the culture medium and optionally further purified.

This invention is further illustrated by the following examples which should not be construed as limiting. The contents of all references, patent applications, patents and published patent applications, cited throughout this application are hereby incorporated by reference.

EXAMPLES

Example 1

Preparation of Chromosomal DNA and Amplification of DNA Fragment by PCR

Chromosomal DNA of *Gluconobacter oxydans* DSM 17078 was prepared from the cells cultivated at 30° C. for 1 day in mannitol broth (MB) liquid medium consisting of 25 g/l mannitol, 5 g/l of yeast extract (Difco), and 3 g/l of Bactopeptone (Difco) by the method described by Sambrook et al (1989) "Molecular Cloning: A Laboratory Manual/Second Edition", Cold Spring Harbor Laboratory Press).

A DNA fragment was prepared by PCR with the chromosomal DNA prepared above and a set of primers, Pf (SEQ ID NO:3) and Pr (SEQ ID NO:4). For the reaction, the Expand High Fidelity PCR kit (Roche Diagnostics) and 10 ng of the chromosomal DNA was used in total volume of 100 µl according to the supplier's instruction to have the PCR product containing SMS 05 DNA sequence (SEQ ID NO:1). The PCR product was recovered from the reaction and its correct sequence confirmed.

Example 2

Disruption of the SMS 05 Gene in *G. oxydans* DSM 17078

The PCR product obtained in Example 1 was cloned in an *E. coli* vector pCR2.1-TOPO and transform *E. coli* TG1 to have a Apr transformant carrying pCR2.1-SMS 05. Then, Kmr cassette isolated from pUC-4K (Amersham Bioscience, accession No. X06404) was inserted into one of the restriction site of the target gene with ligase and resulting ligation product was used to transform *E. coli* TG1 to have Apr Kmr transformant carrying pCR2.1-SMS 05::Km. The pCR2.1-SMS 05::Km plasmid prepared from the transformant was digested by two restriction enzymes selected from the multicloning site of the vector part to isolate a DNA fragment containing SMS 05::Km. The resulting DNA fragment was used to transform *G. oxydans* DSM 17078 by electroporation to have the gene disruptant, *G. oxydans* DSM 17078-SMS 05::Km.

Example 3

Production of Vitamin C from D-Sorbitol, L-Sorbose or L-Sorbosone Using Resting Cells Grown on 3BD Agar Medium Containing 7% L-Sorbose Cells of *G. oxydans* DSM 17078 and *G. oxydans* DSM 17078-SMS 05::Km were grown at 27° C. for 3 days on No. 3BD agar medium containing 70 g/l L-sorbose, 0.5 g/l glycerol, 7.5 g/l yeast extract (Difco), 2.5 g/l MgSO$_4$.7H$_2$O, 10 g/l CaCO$_3$ and 18 g/l agar (Difco).

Cells were scraped from the agar plates, suspended in distilled water and used for resting cell reactions conducted at 30° C. with shaking at 220 rpm. At the conclusion of the incubation period, the reaction mixtures were analyzed by high performance liquid chromatography (HPLC) using an Agilent 1100 HPLC system (Agilent Technologies, Wilmington, USA) with a LiChrospher-100-RP18 (125×4.6 mm) column (Merck, Darmstadt, Germany) attached to an Aminex-HPX-78H (300×7.8 mm) column (Biorad, Reinach, Switzerland). The mobile phase was 0.004 M sulfuric acid, and the flow rate was 0.6 ml/min. Two signals were recorded using an UV detector (wavelength 254 nm) in combination with a refractive index detector. In addition, the identification of the L-ascorbic acid was done using an amino-column (YMC-Pack Polyamine-II, YMC, Inc., Kyoto, Japan) with UV detection at 254 nm. The mobile phase was 50 mM NH$_4$H$_2$PO$_4$ and acetonitrile (40:60).

An Agilent Series 1100 HPLC-mass spectrometry (MS) system was used to identify L ascorbic acid. The MS was operated in positive ion mode using the electrospray interface. The separation was carried out using a LUNA-C8(2) column (100×4.6 mm) (Phenomenex, Torrance, USA). The mobile phase was a mixture of 0.1% formic acid and methanol (96:4). L-Ascorbic acid eluted with a retention time of 3.1 minutes. The identity of the L-ascorbic acid was confirmed by retention time and the molecular mass of the compound.

A series of resting cell reactions (0.5 ml reaction mixture in 5 ml reaction tube) was carried out with 2% D-sorbitol or with 2% L-sorbose, and all reaction mixtures further contained 0.3% NaCl, 1% CaCO$_3$ and cells at a final concentration of 5 absorbance units at 600 nanometers (OD600). After 20 h incubation time, *G. oxydans* DSM 17078 produced 270 mg/l or 670 mg/l of Vitamin C, respectively from 2% D-sorbitol or 2% L-sorbose, respectively. In comparison, strain *G. oxydans* DSM 17078-SMS 05::Km produced 1540 mg/l or 1990 g/l of Vitamin C, respectively.

Example 4

Presence of the SMS 05 Gene and Equivalents in Other Organisms

The presence of SEQ ID NO:1 and/or equivalents showing similarity/identity to SEQ ID NO:1 in other organisms than the ones disclosed herein before, e.g. organisms as mentioned in Table 1, may be determined by a simple DNA hybridization experiment.

Strains of *Acetobacter aceti* subsp. *xylinum* IFO 13693 and IFO 13773 are grown at 27° C. for 3 days on No. 350 medium containing 5 g/l Bactopeptone (Difco), 5 g/l yeast extract (Difco), 5 g/l glucose, 5 g/l mannitol, 1 µl MgSO$_4$.7H$_2$O, 5 ml/l ethanol, and 15 g/l agar. All other *Acetobacter, Gluconacetobacter* and all *Gluconobacter* strains are grown at 27° C. for 3 days on mannitol broth (MB) agar medium containing 25 g/l mannitol, 5 g/l yeast extract (Difco), 3 g/l Bactopeptone (Difco), and 18 g/l agar (Difco). *E. coli* K-12 is grown on Luria Broth agar medium. The other strains/cells are grown on medium recommended by the suppliers or according to methods known in the art. Genomic DNA is extracted as described by e.g. Sambrook et al., 1989, "Molecular Cloning: A Laboratory Manual/Second Edition", Cold Spring Harbor Laboratory Press) from a suitable organism as e.g. mentioned in Table 1.

Genomic DNA preparations are digested with restriction enzymes such as EcoRI or HindIII, and 1 µg of the DNA fragments are separated by agarose gel electrophoresis (1% agarose). The gel is treated with 0.25 N HCl for 15 min and then 0.5 N NaOH for 30 min, and then blotted onto nitrocellulose or a nylon membrane with Vacuum Blotter Model 785 (BIO-RAD Laboratories AG, Switzerland) according to the instruction of the supplier. The resulting blot is then brought into contact/hybridized with a solution wherein the probe, such as e.g. a DNA fragment with SEQ ID NO:1 sequence or a DNA fragment containing the part or whole of the SEQ ID NO:1 sequence to detect positive DNA fragment(s) from a test organism. A DIG-labeled probe, e.g. SEQ ID NO:1, may be prepared according to Example 1 by using the PCR-DIG labeling kit (Roche Diagnostics) and a set of primers, SEQ ID NO:3 and SEQ ID NO:4. A result of such a blot is depicted in Table 1.

The hybridization may be performed under stringent or highly stringent conditions. A preferred, non-limiting example of such conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C. Highly stringent conditions include, for example, 2 h to 4 days incubation at 42° C. in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 min in 2×SSC and 0.1% SDS at room temperature and then washing twice for 15-30 min in 0.5×SSC and 0.1% SDS or 0.1×SSC and 0.1% SDS at 65-68° C. To detect DNA fragments with lower identity to the probe DNA, final washing steps can be done at lower temperatures such as 50-65° C. and for shorter washing time such as 1-15 min.

The genes corresponding to the positive signals within the respective organisms shown in Table 1 can be cloned by a PCR method well known in the art using genomic DNA of such an organism together with a suitable primer set, such as e.g. SEQ ID NO:3 and SEQ ID NO:4 under conditions as described in Example 1 or as follows: 5 to 100 ng of genomic DNA is used per reaction (total volume 50 µl). Expand High Fidelity PCR system (Roche Diagnostics) can be used with reaction conditions consisting of 94° C. for 2 min; 30 cycles of (i) denaturation step at 94° C. for 15 sec, (ii) annealing step at 60° C. for 30 sec, (iii) synthesis step at 72° C. for 0.5 to 5 min depending to the target DNA length (1 min/1 kb); extension at 72° C. for 7 min. Alternatively, one can perform a PCR with degenerate primers, which can be synthesized based on SEQ ID NO:2 or amino acid sequences as consensus sequences selected by aligning several amino acid sequences obtained by a sequence search program such as BLASTP (or BLASTX when nucleotide sequence is used as a "query sequence") to find proteins having a similarity to the protein of SEQ ID NO:2. For PCR using degenerate primers, temperature of the second annealing step (see above) can be lowered to 55° C., or even to 50-45° C. A result of such an experiment is shown in Table 1.

Samples of the PCR reactions are separated by agarose gel electrophoresis and the bands are visualized with a transilluminator after staining with e.g. ethidium bromide, isolated from the gel and the correct sequence is confirmed.

Consensus sequences mentioned above might be amino acid sequences belonging to certain categories of several protein domain/family databases such as PROSITE (database of protein families and domains), COGs (Cluster of Ortholog Groups), CDD (Conserved Domain Databases), pfam (large collection of multiple sequence alignments and hidden Markov models covering many common protein domains and families). Once one can select certain protein with identical/similar function to the protein of this invention from proteins containing domain or family of such databases, corresponding DNA encoding the protein can be amplified by PCR using the protein sequence or its nucleotide sequence when it is available in public databases.

Example 5

Disruption of the SMS 05 Gene and Equivalents in Other Organisms for Production of Vitamin C In order to improve Vitamin C production in a suitable microorganism which is capable to directly produce Vitamin C from a given substrate, the SMS 05 gene and equivalents as e.g. a PCR product obtained in Example 4, referred to hereafter as gene X, can be disrupted in accordance to the SMS 05 gene in *G. oxydans* DSM 17078 (see Example 2) to generate a knockout mutant carrying SMS 05 equivalent gene::Km. Suitable host strains for generation of such knockout mutants may be selected from e.g. *Gluconobacter* strains listed in Table 1, in particular e.g. *G. oxydans* IFO 3293, *G. oxydans* IFO 3292, *G. oxydans* ATCC 621H, *G. oxydans* IFO 12528, *G. oxydans* IFO 3291, *G. oxydans* IFO 3255, *G. oxydans* IFO 3244, *G. cerinus* IFO 3266, *G. frateurii* IFO 3260, *G. oxydans* IFO 3287, *Acetobacter aceti* subsp. *orleanus* IFO 3259, *Acetobacter aceti* subsp. *xylinum* IFO 13693, *Acetobacter aceti* subsp. *xylinu* in IFO 13773 and *Acetobacter* sp. ATCC 15164.

The knockout mutant such as, e.g. a knockout mutant *G. oxydans* IFO 3293-SMS 05 equivalent gene::Km can be generated as follows: the PCR product obtained in Example 4 is cloned in an *E. coli* vector pCR2.1-TOPO and used to transform *E. coli* TG1 to have a Apr transformant carrying pCR2.1-gene X. Then, Kmr cassette isolated from pUC-4K (Amersham Bioscience, accession No. X06404) is inserted into one of the restriction site of the target gene with ligase and the resulting ligation product is used to transform *E. coli* TG1 to have Apr Kmr transformant carrying pCR2.1-gene X::Km. The pCR2.1-gene X::Km plasmid prepared from the transformant is digested by two restriction enzymes selected from the multi-cloning site of the vector part to isolate a DNA fragment containing gene X::Km. The resulting DNA fragment is used to transform the host strain carrying the SMS 05 equivalent gene by electroporation to have the gene disruptant carrying SMS 05 equivalent gene::Km.

Further modifications including genes involved in the conversion of D-sorbitol, L-sorbose and/or L-sorbosone into Vitamin C within said strains may be generated to improve Vitamin C production by such strains.

Production of Vitamin C using the cells of the knockout mutant, e.g. *G. oxydans* IFO 3293-SMS 05 equivalent gene::Km, and the corresponding wild-type strain, e.g. *G. oxydans* IFO 3293, are performed according to Example 3.

In the resting cell reaction with 1% L-sorbosone as the substrate, the mutant strain can produce at least more than 20% Vitamin C compared to the wild-type strain.

TABLE 1

Equivalents of the SMS 05 gene in other organisms.

| Strain | Signal 1 | Signal 2 | Signal 3 |
|---|---|---|---|
| *G. oxydans* DSM 17078 | + | + | + |
| *G. oxydans* IFO 3293 | + | + | + |
| *G. oxydans* IFO 3292 | + | + | + |
| *G. oxydans* ATCC 621H | + | + | + |
| *G. oxydans* IFO 12528 | + | + | + |
| *G. oxydans* G 624 | + | + | + |
| *G. oxydans* T-100 | + | + | + |
| *G. oxydans* IFO 3291 | + | + | + |
| *G. oxydans* IFO 3255 | + | + | + |
| *G. oxydans* ATCC 9937 | + | + | + |
| *G. oxydans* IFO 3244 | + | + | + |
| *G. cerinus* IFO 3266 | + | + | + |
| *G. frateurii* IFO 3260 | + | + | + |
| *G. oxydans* IFO 3287 | + | + | + |
| *Acetobacter aceti* subsp. *orleanus* IFO 3259 | + | + | + |
| *Acetobacter aceti* subsp. *xylinum* IFO 13693 | + | + | + |
| *Acetobacter aceti* subsp. *xylinum* IFO 13773 | + | + | + |
| *Acetobacter sp.* ATCC 15164 | + | + | + |
| *G. thailandicus* NBRC 100600 | + | + | + |
| *Gluconacetobacter liquefaciens* ATCC 14835 | + | + | + |
| *Sinorhizobium meloloti* 1021 | − | − | + |
| *Brucella suis* 1330 | − | − | + |
| *Brucella melitensis* 16M | − | − | + |
| *E. coli* | − | − | − |
| *Saccharomyces cerevisiae* | − | − | − |
| *Aspergillus niger* | − | − | − |
| Mouse | − | − | − |

Signal 1: Detection of DNA on a blot with genomic DNA of different strains and SEQ ID NO:1 as labeled probe.
Signal 2: Detection of DNA of different strains in a PCR reaction using primer pair SEQ ID NO:3 and SEQ ID NO:4.
Signal 3: Detection of DNA of different strains in a PCR reaction using degenerate primers.
For more explanation refer to the text.

The invention claimed is:

1. A process for production of Vitamin C with a microorganism selected from *Gluconobacter*, wherein said process comprises:
   (a) cultivating said microorganism in an aqueous nutrient medium under conditions such that Vitamin C from D-sorbitol or L-sorbose is produced by direct fermentation and
   (b) optionally isolating Vitamin C as a fermentation product;
   wherein a gene encoding NAD(P) dependent L-sorbosone dehydrogenase is knocked-out in said microorganism, and wherein said gene when not knocked-out comprises a polynucleotide selected from the group consisting of:
   (i) polynucleotides encoding a polypeptide comprising the amino acid sequence set forth in SEQ ID NO: 2;
   (ii) polynucleotides comprising the nucleotide sequence set forth in SEQ ID NO: 1; and
   (iii) polynucleotides obtainable by nucleic acid amplification using genomic DNA from a *Gluconobacter* as a template and primers comprising SEQ ID NO: 3 and SEQ ID NO: 4, and encoding a polypeptide having L-sorbosone dehydrogenase activity.

2. The process according to claim 1, wherein said polynucleotide encodes a polypeptide comprising the amino acid sequence set forth in SEQ ID NO: 2.

3. The process according to claim 1, wherein said polynucleotide is obtainable by nucleic acid amplification using said genomic DNA as a template and primers comprising SEQ ID NO: 3 and SEQ ID NO: 4, and encoding a polypeptide having NAD(P) dependent L-sorbosone dehydrogenase activity.

4. The process according to claim 1, wherein said microorganism is selected from the group consisting of *Gluconobacter frateurii*, *Gluconobacter cerinus*, *Gluconobacter thailandicus*, and *Gluconobacter oxydans*.

5. The process according to claim 1, wherein said microorganism is selected from the group consisting of *Gluconobacter oxydans* and *Gluconobacter oxydans* DSM 17078.

6. The process according to claim 1, wherein Vitamin C from D-sorbitol or L-sorbose is produced in quantities of 1000 mg/l or more when measured in a resting cell method after an incubation period of 20 hours.

7. The process according to claim 1, wherein at least 500% more Vitamin C from 2% D-sorbitol is produced in a resting cell method after an incubation period of 20 hours compared to the amount of Vitamin C produced under these conditions in a microorganism expressing said gene encoding NAD(P) dependent L-sorbosone dehydrogenase.

* * * * *